(12) United States Patent
Zantl (10) Patent No.: US 9,778,153 B2
(45) Date of Patent: *Oct. 3, 2017

(54) MICROFLUID DEVICE AND METHOD OF PRODUCING DIFFUSIVELY BUILT GRADIENTS

(71) Applicant: IBIDI GMBH, Martinsried (DE)

(72) Inventor: Roman Zantl, Baldham (DE)

(73) Assignee: IBIDI GMBH, Martinsried (DE)

( * ) Notice: Subject to any disclaimer, the term of this patent is extended or adjusted under 35 U.S.C. 154(b) by 124 days.

This patent is subject to a terminal disclaimer.

(21) Appl. No.: 14/101,928

(22) Filed: Dec. 10, 2013

(65) Prior Publication Data

US 2014/0141464 A1 May 22, 2014

Related U.S. Application Data

(63) Continuation of application No. 11/481,557, filed on Jul. 5, 2006, now Pat. No. 8,679,737.

(30) Foreign Application Priority Data

Jul. 5, 2005 (EP) ........................... 5014563

(51) Int. Cl.
*G01N 1/30* (2006.01)
*C12Q 1/00* (2006.01)
*B01F 13/00* (2006.01)
*B01F 15/04* (2006.01)
(Continued)

(52) U.S. Cl.
CPC ........... *G01N 1/30* (2013.01); *B01F 13/0059* (2013.01); *B01F 13/0093* (2013.01); *B01F 15/0404* (2013.01); *B01L 3/502707* (2013.01); *B01L 3/502746* (2013.01); *B01L 3/502769* (2013.01); *C12Q 1/34* (2013.01); *B01L 3/5025* (2013.01); *B01L 2300/0816* (2013.01); *B01L 2300/0867* (2013.01); *B01L 2400/0406* (2013.01); *B01L 2400/0472* (2013.01)

(58) Field of Classification Search
CPC .......................... B01F 13/059; B01F 13/0093; B01F 15/0404; B01L 3/502707; B01L 3/502746; B01L 3/502749; B01L 3/5025; B01L 2300/0816; B01L 2300/0867; B01L 2300/0406; B01L 2300/0472; C12Q 1/34; G01N 1/30

See application file for complete search history.

(56) References Cited

U.S. PATENT DOCUMENTS 8,679,737 B2 * 3/2014 Zantl ................................ 435/4

* cited by examiner

*Primary Examiner* — Michael Hobbs
(74) *Attorney, Agent, or Firm* — Moore & Van Allen PLLC; Henry B. Ward, III (57) ABSTRACT

A microfluid device for producing diffusively built gradients comprising a bottom plate and a cover plate, wherein the cover plate has recesses and is connected to the bottom plate in a liquid-tight manner so that the recesses form at least two reservoirs and one observation chamber, which connects the reservoir, a reservoir can be filled particularly through an inlet/outlet through the cover plate, and the cross-sectional surface of the observation chamber is at least 5 times, preferably at least 200 times smaller at the aperture of the observation chamber into one of the reservoirs than the maximum cross-sectional surface of the reservoir in parallel to this cross-sectional surface of the observation chamber.

18 Claims, 8 Drawing Sheets

(51) Int. Cl.
*C12Q 1/34* (2006.01)
*B01L 3/00* (2006.01)

MICROFLUID DEVICE AND METHOD OF PRODUCING DIFFUSIVELY BUILT GRADIENTS

CROSS-REFERENCE TO RELATED APPLICATIONS

This document is a continuation of U.S. patent application Ser. No. 11/481,557, which was filed on Jul. 5, 2006, now U.S. Pat. No. 8,679,737, which issued on Mar. 25, 2014, which in turn claims priority from European Patent Application No. EP 5014563, which was filed on Jul. 5, 2005, now EP 1 741 487, issued Mar. 9, 2011.

BACKGROUND OF THE INVENTION

The present invention refers to a microfluid device and a method of producing diffusively built gradients, particularly in the field of microfluidics.

Concentration gradients of certain substances in liquid media are of decisive meaning in many applications. It is for instance known that a defined pH gradient is required for the isoelectric focusing of proteins.

In the field of cytology, defined concentration courses are of decisive meaning for research. The precise concentration for instance, at which a substance acts toxically on a cell culture, can be determined in that a continuous concentration increase of the substance to be examined is built up in the culture medium over a homogeneous cell layer.

A defined and long-term stable (over several hours to days) gradient is also required to examine the chemotactic behavior of slow cells, e.g. in that the migration of cells is observed at a mean velocity of e.g. 20 µm/h in or against the direction of a concentration gradient. Some differentiations of cells in living organisms have for instance the capability of moving in the direction of the source (point or space of high concentration compared to the depression, a point or space of low concentration) of determined substances, which is generally termed as "chemotaxis". In this manner, leucocytes may for instance accumulate at foci of inflammation and vascular precursor cells may form new vessels in the regions which are undersupplied for instance with oxygen or nutriments. The prevention of this mechanism is a promising approach in the control of rapidly growing tumors. It could be attempted to prevent the supply with nutriments and oxygen in excrescent tissue. Furthermore, chemotaxis of tumor cells plays an important role in metastasis. Thus, particularly quantitative measurements of the chemotactic behavior of cells of the human body are of interest, which move at a speed of approx 20 µm per hour towards the source of the messenger.

In order to obtain significant data it is assumed that preferably paths of cells of approximately 20 times the cell diameter are to be observed. Typical cell diameters are between 5 µm and 30 µm. To cover for instance 600 µm, a cell with a mean velocity of 20 µm/h needs 30 hours, which corresponds to a typical observation period.

The prior art concerned with the structure of a concentration gradient will now be explained by means of the structure in experiments for chemotactic examinations.

The chamber developed by Boyden (Boyden, S., 1962: "The chemotactic effect of mixtures of antibody and antigen on polymorphonuclear leucocytes", J Exp Med 115: 453-466) has been in use in various forms up to the present day. In this system a porous membrane separates two chambers in which different concentrations of chemokines are located. A step-like to sigmoid concentration gradient forms in the membrane area. The cells are applied onto one side of the membrane and actively move to the other side in that they migrate through the pores. After a determined period of time, the chamber is removed, the filter is removed and the cells are counted after a dyeing step on the upper and lower side of the membrane.

The difficulty of the evaluation is the distinction between chemotaxis and increased random movement (chemokinese). It may also happen that migrated cells detach from the membrane surface, thus falsifying the result. Only by means of parallel supervision can it be verified whether the cells have actually reacted on stimulus and have therefore migrated or whether they merely randomly moved to the other side of the membrane. Microscopic observations of the cells during the experiment are not possible.

A further method is the use of microcapillaries. In this system a microcapillary with a microscopically small opening is moved in the proximity of the cells that are located in a cell vessel. The opening of the capillaries and the medium surrounding the cells are fluidically connected to one another (Gerisch and Keller, 1981). The chemokine diffuses or flows out of the opening of the capillaries that is located in the proximity of the cell or a cell compound.

The capillaries are of glass and must therefore be handled with care. Furthermore, a micro-manipulator is required for handling the capillaries in the proximity of the cells. A further disadvantage of this system is the high costs and the inconvenience in application. Moreover, the radial form of the gradient around the capillary opening is only suitable for the simultaneous observation of single or few cells. The gradient may be adjusted in a locally very steep manner. The form and time response of the gradient are complex and cannot be quantified. Smaller flows within the cell culture vessel also lead to massive concentration changes that cannot be quantified. Such flows may for instance be caused by convection.

Quantitative statements about the migration behavior of many cells are generally possible by several parallel experiments only, which, however cannot be carried out identically due to the complex handling and which can therefore not be compared to one another. Furthermore, image processing is required for the evaluation of the data.

The Zigmond chamber (Zigmond, S. H., 1977: "Ability of polymorphonuclear leukocytes to orient in gradients of chemotactic factors". J Cell Biol 75: 606-16; Zigmond, D. H., 1988: "Orientation chamber in chemotaxis", Methods in enzymology 162: 65-72) is composed of two chambers that are separated between the chambers by a thin observation volume. The observation volume is restricted from the top by a cover glass, which is mounted by suitable mechanical attachment at a defined distance from the surface. The water level in the two chambers must possibly precisely correspond to the height of the cover glass. Identical cell culture medium is located in both chambers, wherein a defined amount of the chemokine is added to one of the chambers. A linear chemical gradient is formed by diffusion in the ideal case. The use of the cover glass enables to microscopically follow the chemotactic movement of the cells.

A restriction for such examinations is that cells can only react to gradients if the concentration drop over a cell length is approximately 1% of the mean concentration at the location of the cell. That means that the gradient must be sufficiently steep. By diffusion and undesired flow the gradient in real Zigmond chambers is for approximately 30 to 60 minutes sufficiently steep for chemotaxis studies. After that it is too flattened or interfered by flows. Moreover, the application of the Zigmond chambers demands great skill in the performance of the respective tests, since liquid flows can quickly destroy the gradient due to the multipiece structure and the open chambers.

The Dunn chamber (Zicha, D. G. A. Dunn and A. F. Brown, 1991: "A new direct-viewing chemotaxis chamber", J Cell Sci 99 (Pt 4): 769-75) is a further development of the Zigmond chamber. The two portions that contain or not contain the chemokine are arranged radially with respect to one another and are separated from one another by a closed, annular barrier. After putting on the cover glass, the gap serving for examination is located between the annular barrier and the cover glass so that it can be examined whether the cells extend in an aimed manner e.g. towards the center of the arrangement if the chemokine is added in the central portion.

The Dunn chamber allows the chemotactic examination over longer periods of time than the Zigmond chamber. The geometry in this case is disadvantageous, since the direction of the chemotactic movement to be expected depends on the location within the gap. This makes the valuation of the data more complex. Moreover, the chemical gradient is very instable compared to mechanical influences, such as holding the chamber at an oblique angle, which amongst others leads to an interference of the diffusive gradient caused by the additionally occurring flow.

The chemotactic behavior of the respective cell type does generally not only depend on the substance but also on its concentration and steepness of the concentration decline. The standard value for the concentration decline that can just about be detected by the cell may be—as already mentioned above—about 1% decline per cell length at the location of the cell.

Chemotactically active cells, such as human umbilical vein endothelial cells (HUVEC), which amongst others react to the substance VEGF (vascular endothelial growth factor) and the tumor cell line HT1080, which chemotactically reacts to FCS (fetal calf serum) serve as an example for cells.

Due to the above described disadvantages in the prior art, it is the object of the invention to provide a microfluid device and a method of producing diffusively built gradients, wherein the microfluid device and the method prevent the interferences of the gradient by pressure fluctuations and/or flow in the microfluid device.

BRIEF SUMMARY OF THE INVENTION

This object is solved by a microfluid device according to claim 1 and by a method according to claim 16.

The microfluid device for generating diffusively built gradients according to the invention comprises a bottom plate and a cover plate, wherein the cover plate has recesses and is connected in a liquid-tight manner with the bottom plate so that the recesses form at least two reservoirs and an observation chamber, which connects the reservoirs, a reservoir can be filled particularly by an inlet/outlet through the cover plate, and wherein the cross-sectional surface of the observation chamber at the aperture of the observation chamber into one of the reservoirs is at least 5 times smaller, particularly at least 20 times smaller than the maximum cross-sectional surface of the reservoir parallel to this cross-sectional surface of the observation chamber.

The cross-sectional surface of the observation chamber may preferably be at least 10 times, particularly at least 30 times smaller at the aperture of the observation chamber into one of the reservoirs than the maximum cross-sectional surface of the reservoir parallel to this cross-sectional surface of the observation chamber.

A diffusively building up gradient or a diffusively built gradient is a concentration gradient, which, caused by different concentrations in two chambers (e.g. two reservoirs) builds up or has built up in a third chamber (e.g. an observation chamber) between the two chambers, and which is generated by the diffusion between the two chambers (which serve as source and depression). For a gradient that builds up diffusively, further flow between the spaces should preferably not take place in addition to the diffusion (pressure fluctuations may for instance cause an additional flow and destroy the diffusive gradient formation).

If the cross-sectional surface of a reservoir is not constant, the aperture is the point at which the cross-sectional surface of the reservoir continuously or discontinuously reaches a smallest value, namely the value for the cross-sectional surface of the observation chamber at the aperture. If for instance a reservoir has a cylindrical shape and the observation chamber opens into the curved side wall of the reservoir, the (planar) cross-sectional surface of the observation chamber is restricted by the intersecting line of the observation chamber with the cylinder. Accordingly, the cross-sectional surface of the observation chamber is also determined in the case of other curved reservoir surfaces.

Generally, a reservoir of the microfluid device according to the invention can be filled if a liquid and/or cells can be filled into the reservoir.

The bottom plate and the cover plate are connected in a liquid-tight manner, which means that liquid cannot enter or escape at its connection points.

The microfluid device according to the invention is advantageous compared to the prior art, since the liquid-tight connection between the bottom and cover plate and the different sizes of the cross-sectional surfaces of the reservoir enable a long-time stable diffusion from the source to the depression, compared to the observation chamber.

A reservoir may for instance contain a defined concentration of a chemical substance so that this reservoir serves as a source for this substance. The second reservoir may have a significantly lower concentration of the chemical substance and serves as a depression of this substance. The reservoirs are arranged at opposing sides of the observation chamber. Due to the much larger cross section of the reservoir compared to the cross section of the observation chamber, it is now possible that between the source and the depression a linear, long-time stable concentration drop can build up by diffusion of the chemical substance.

A further advantage compared to the Zigmond chamber is that—although the bottom plate is connected to the cover plate—a reservoir of the microfluid device can still be filled and thus a more simple and flexible implementation of experiments is enabled.

The bottom of the observation chamber and the bottom of at least one reservoir are preferably arranged on one level.

The cross-sectional surfaces of the observation chamber may particularly at least at two apertures into one reservoir be at least 5 times smaller, particularly at least 10 times smaller than the maximum cross-sectional surface of the reservoir in parallel to this cross-sectional surface of the observation chamber. The cross-sectional surfaces of the observation chamber may preferably on at least two openings into one reservoir be at least 20 times smaller, particularly at least 30 times smaller than the maximum cross-sectional surface of the reservoir in parallel to this cross-sectional surface of the observation chamber.

In a preferred development, the bottom plate or the lower side of the bottom plate of the microfluid device may be planar, and particularly the bottom plate may be the bottom of the reservoirs, the observation chamber and possible channels of the microfluid device. A bottom plate may preferably be a sheet, and the bottom plate may particularly have a thickness between 0.2 μm and 2 mm. Preferably it has the base of a conventional object carrier, e.g. 25.5 mm×75.5 mm, and the bases of the bottom plate and the cover plate may particularly be identically large.

The cover plate may preferably be planar, particularly in the area of an inlet/outlet. Moreover, the cover plate may have a thickness of between about 0.5 mm and 3 mm, preferably 1.5 mm. Particularly, the bottom and the cover plate may be connected in a liquid-tight and/or airtight manner. The volume of the reservoir may be in the range of 5 μl to 1000 μl, preferably between 100 μl and 500 μl, particularly 300 μl.

An observation chamber may have a polygonal base surface as a bottom and as a cover, and particularly the bottom and/or the cover may be planar. The bottom is formed by the bottom plate of the microfluid device, and the cover is formed by the cover plate of the microfluid device. Preferably at least two sides of an observation chamber may be connected to one reservoir. It is possible that the entire surface of one side of the observation chamber serves as an opening to the reservoir, that means that this side of the observation chamber is completely open. The height of the observation chamber (distance between the bottom and the cover) may preferably be between 10 μm and 500 μm, particularly 75 μm, the width may preferably be approximately 30 μm to 1 cm, particularly 1 mm, and the length (distance between the aperture planes of the reservoirs) may be approximately 100 μm to 5 mm, particularly approximately 500 μm to 3 mm or approximately 1 mm to 2 mm.

In a preferred embodiment, the observation chamber may be a small channel, gap or a capillary with a preferably small height. Thus, it is possible to obtain an advantageous, large observation surface with a possibly low substance transport. This leads to a virtually two-dimensional diffusion and thus to simplified observation possibilities. If a small or narrow channel is used as observation chamber, the substance transport may run through this channel and the degradation of the gradient may take place very slowly. The height of the reservoirs is typically significantly larger than the one of the observation chamber so that the concentration of the diffusively transported substances can be quickly and severely diluted on the side that serves for concentration depression.

The volume of at least one reservoir may preferably at least be 50 times larger, particularly more than 100 times larger. The volume of at least one reservoir may preferably be at least 200 times, particularly at least 500 times, and preferably at least 1000 times larger than the volume of the observation chamber.

In a preferred development, the cross-sectional surface of the observation chamber may be between 0.05 mm$^2$ and 0.4 mm$^2$, preferably between 0.075 mm$^2$, and 0.1 mm$^2$, and/or the cross-sectional surface of a reservoir may be between 0.25 mm$^2$ and 8 mm$^2$, preferably between 0.37 mm$^2$ and 2 mm$^2$.

The cross-sectional surface of a reservoir may preferably be between 0.25 mm$^2$ and 2 mm$^2$, particularly between 0.37 mm$^2$ and 0.5 mm$^2$, if the cross-sectional surface of the observation chamber at the aperture of the observation chamber into the reservoir is at least 5 times smaller than the cross-sectional surface of the reservoir parallel to this cross-sectional surface of the observation chamber. If the above cross-sectional surface of the observation chamber is at least 20 times smaller than the above-mentioned cross-sectional surface of the reservoir, the cross-sectional surface of the reservoir may be between 1 mm$^2$ and 8 mm$^2$, particularly between 1.5 mm$^2$ and 2 mm$^2$.

If the above cross-sectional surface of the observation chamber is at least 10 times smaller than the above described cross-sectional surface of the reservoir, the cross-sectional surface of the reservoir may preferably be between 0.5 mm$^2$ and 4 mm$^2$, particularly between 0.75 mm$^2$ and 1 mm$^2$. If the above cross-sectional surface of the observation chamber is at least 30 times smaller than the above described cross-sectional surface of the reservoir, the cross-sectional surface of the reservoir may preferably be between 1.5 mm$^2$ and 12 mm$^2$, particularly between 2.25 mm$^2$ and 3 mm$^2$.

In an advantageous development, at least two, particularly three channels may lead into a reservoir. The reservoir may preferably be cuboidal, and the channel may particularly be arranged in parallel to another and may lead into the same reservoir side. This reservoir side may preferably be located opposite to the reservoir side which abuts on the observation chamber. The channels may particularly have inlets/outlets.

The above development is advantageous, since due to the open inlets/outlets of the channels, a flow in the channel structure can be controlled, without generating a flow in the observation chamber. Thus, concentrations or concentration fluctuations in the channel structure may be controlled and/or prevented.

Additionally, each reservoir may have at least one loackable and/or fillable inlet/outlet, the inlet/outlet may particularly be lockable in a liquid-tight and/or air-tight manner and preferably leads through the cover plate into a reservoir. The reservoir can be filled by an inlet/outlet, particularly by a liquid, or a liquid may escape from the reservoir or may be removed therefrom. An inlet/outlet may particularly have the shape of a through hole through the cover plate into a reservoir. The inlets/outlets of a reservoir may preferably be lockable in an air-tight manner. Within small volumes the aqueous liquids may virtually be incompressible so that pressure fluctuations occurring can hardly cause any liquid movements. Generally, an inlet/outlet may comprise a channel that is formed by a recess in the cover plate together with the bottom plate.

An inlet/outlet may have a minimal cross-sectional surface of between 0.03 mm$^2$ and 13 mm$^2$, particularly between 0.2 mm$^2$ and 3.2 mm$^2$. The cross-sectional surface of an inlet/outlet may particularly vary, e.g. in the case of a conically shaped inlet/outlet the minimal cross-sectional surface is the smallest cross-sectional surface that the conical inlet/out has. The cross-sectional surface of an inlet/outlet may particularly be constant, e.g. the dimensions of an inlet/out with constant, e.g. rectangular, cross-sectional surface may be 300 μm×100 μm to 2 mm×0.5 mm. An inlet/outlet with a round cross-sectional surface may have a diameter of e.g. between 0.3 mm to 4 mm, particularly between 0.5 mm and 2 mm.

Furthermore, an inlet/outlet, particularly in addition to a channel, may have openings, e.g. conical pots (particularly with a height of up to 7 mm and a diameter of up to 2 mm in the mean cross section) for the insertion of e.g. pipette tips or for attaching hoses or pumps. The inlets/outlets may also be formed such that a small drop that is applied onto the inlet, is drawn into the reservoir. Caused by the fact that the at least one inlet/outlet can be locked, any flow through the observation chamber and thus the destruction of the gradient is prevented.

The above described inlet/outlet with its small cross-sectional surfaces reveals a further advantage compared to existing Zigmond and Dunn chambers. In the simplest case the inlets/outlets may be locked in a liquid-tight and/or air-tight manner by vacuum grease or an adhesive film (such as Scotch tape). They can also be locked by matching covers or plugs. The locking by covers may, however, lead to pressure fluctuations and thus to a flow within the microfluid device. To prevent this, a cover may for instance be made of one piece, which simultaneously locks all inlets/outlets and other openings, such as possible through holes.

Furthermore, a through hole through the cover plate and/or bottom plate into the observation chamber may be provided. The through hole may also be formed in the shape of an elevation (such as a conical fixture, which is irreversibly connected to the cover plate) or the complete cover plate may be formed in the area of the observation chamber as a through hole. Through such a through hole, particularly a gel (to reduce the diffusion velocity and thus to particularly stabilize the gradient) or particularly spheroids can be filled. Spheroids are usually flattened, spherical cell clusters with a diameter of 100 μm to 1 mm, which can be formed by respective preparation from a plurality of cell types. The filling-in of the spheroids compared to the filling with single cells may have the advantage that the cells at the beginning of the experiment are concentrated at one point, which leads to a simpler symmetry of the system. If the cells move from the symmetry point preferably in one direction, this can immediately be recognized without further evaluation.

In a preferred embodiment, the bottom plate and the cover plate may irreversibly be connected to one another, particularly the bottom plate and the cover plate may be adhered to one another, they may be ultrasound-bonded or they may be bonded by heat or a solvent (see e.g. DE 101 30 428 A1).

The bottom plate may particularly at least in the area of the observation chamber be composed of an optically high-quality material. Optically high-quality materials have a lower birefringence and a lower fluorescence, which is particularly advantageous in fluorescence microscopy. In a further embodiment, the entire bottom plate and/or the cover plate may consist of an optically high-quality material. The refractive index of the materials is for optical analysis preferably between 1.2 and 1.6.

In a special embodiment, the reservoirs may also be located at opposing sides of the observation chamber. This may enhance a regular diffusion from the reservoir serving as a source to the reservoir serving as a depression.

Furthermore, the microfluid device may additionally have at least one channel with at least one inlet/outlet, wherein the channel leads into the observation chamber and particularly the bottom of the channel may be located on the same plane as the bottom of the observation chamber. The at least one inlet/outlet may have the same structures and dimensions as an inlet/outlet of a reservoir. The channel may for instance have a width of 0.5 mm and may particularly have the same height as the observation chamber. Via this channel the observation chamber may for instance be filled with cells. Additionally, a channel with e.g. the same dimensions may open into the opposing side. In this manner, an intersecting channel may be produced, in which the molecules or cells can be flushed-in even after establishment of the gradient into the observation chamber. Under these circumstances, significant examinations can be carried out only after a respective waiting period, after which the quasi-statical state in the observation chamber was established.

The channel may particularly lead via one side of the observation chamber into the observation chamber, wherein the observation chamber does not adjoin a reservoir at this side.

The microfluid device may for instance comprise two reservoirs and one observation chamber between the reservoirs, wherein one channel leads perpendicularly with respect to both reservoirs into the observation chamber. A possible second channel may preferably open into the observation chamber at the opposing side of the aperture of the first channel and may particularly also be provided perpendicularly with respect to the two reservoirs, so that both channel may form an intersecting channel.

When dimensioning channels it must generally be taken into consideration that capillary effects may occur in the case of specific dimensions so that a liquid gets caught in the channel.

In a specific embodiment, the height and/or width of the observation chamber and/or of the reservoirs of the microfluid connection may preferably be constant. Particularly, the observation chamber may have a height between 0.05 mm and 0.15 mm and a width between 0.15 mm and 5 mm, and particularly at least one reservoir may have a height between 0.5 mm and 1 mm and a width between 4 mm and 9 mm.

The observation chamber and/or the reservoirs may in a specific embodiment have the shape of an even prism with an even number of sides. "An even prism with an even number of sides" means that the side walls of the prism are perpendicular with respect to the even numbered polygonal base and cover face of the prism, that means that the cover face lies in parallel to the base face and the number of the rectangular side walls is even. Preferably, the observation chamber and/or the reservoirs may have a cuboidal shape.

In particular, the microfluid device may at least comprise two further reservoirs, wherein the reservoirs are arranged at the sides of the observation chamber such that two reservoirs each oppose one another. In order to be able to directly compare the strength of the influence of different substances onto the chemotactic behavior, reservoirs may be filled in this manner by different substances which may produce gradients in different directions in the observation chamber.

The microfluid device may preferably have at least one cell adhesion surface in the observation chamber. The cell adhesion surface may be realized in the form of a surface structuring, e.g. by plasma treatment or ultrasonic illumination by the aid of a mask procedure, and/or by a surface treatment, e.g. by coating with adhesion proteins or peptides by means of array plotting. The one or plurality of cell adhesion surfaces may particularly on the whole be smaller than the bottom of the observation chamber. Cell adhesion surfaces may facilitate the evaluation of the chemotactic assay.

An example for a respective embodiment is a rectangular observation chamber bottom surface, particularly having the size of 1 mm×2 mm, wherein the longer edges of the surface are each connected with a reservoir in the aperture plane. Oblong rectangular portions, particularly each of 100 μm×500 μm, are treated for cell adhesion in parallel to the shorter edges, i.e. in the direction of the expected chemotactic migration. The remaining surface of the observation area is not surface treated and further and does therefore not allow any cell adhesion. If the cells are now flushed into the observation surface, the cells accumulate in a statistically distributed manner on the oblong rectangular adhesion portions. After carrying out the chemotaxis experiment, migration can be observed by a significant increase of the cell density in the direction towards the reservoir which represents the source, contrary to a significantly lower cell density in the direction of the reservoir which represents the depression.

In a different, possible surface structuring and/or treatment, the adhesion surface may for instance be as broad as an adhered cell. Depending on the cell type, the cell diameter is between 5 µm and 20 µm. This structure may particularly be advantageous if the chemotaxis of cells is to be examined that significantly react on cell contacts among one another. Human endothel cells for instance show a stronger directed reaction to the same cells than to chemical gradients, which aggravates evaluation of the experiments. Preferably the cells may be arranged in a manner strung up on beads in one row and only move towards and away from the source. This design may then serve for the general evaluation of whether the cells show chemotaxis.

Furthermore, the microfluid device may have at least one rectangular, rhombical, triangular or round cell adhesion surface. The rhombical and triangular adhesion surfaces may point with one corner towards the reservoir, which represents the source. If the cells concentrate in this corner, chemotaxis can easily be verified by image processing evaluation.

The microfluid device preferably comprises at least one marking in the observation chamber to determine the location and/or velocity of migrating cells. The marking may be pressed in, printed on, painted on, lasered in etc. and may particularly serve for specifying a diffusion in the observation chamber. The markings may have a size of particularly 1 µm to 100 µm and their distance to one another may be between 10 µm to 1 mm.

In a further embodiment, the observation chamber may have structures or materials such as collagen or matrigel in the aperture plane to the reservoirs. These structures or materials may reduce the diffusion velocity and thus particularly keep the gradient stable for a longer period of time. The cells may also be filled into a gel matrix such as matrigel instead of a liquid medium to even better simulate the relations in the human an animal body.

The invention further provides an analysis system, which comprises the microfluid device according to the invention and a read-out device, particularly microscopes or electrode arrays.

In a further embodiment, electrodes can be attached in or on the observation chamber to support the gradient. Many biologically relevant molecules carry a charge, which can be utilized to generate concentration gradients by utilizing electrodes or to further stabilize the gradients.

The microfluid device according to the invention may generally be composed of plastics, such as e.g. PC (polycarbonat), PS (polystyrene), PE (polyethylene), PVC (polyvinylchloride), COC (cyclo-olefin copolymer), COP (cyclo-olefin polymer), PMMA (polymethylmethacrylat) etc. Depending on the application, gas-permeable or gas-impermeable plastics may be used.

An especially preferred embodiment is an arrangement for generating diffusively built gradients with at least two of the above-mentioned microfluid devices, wherein the at least two bottom plates are formed as one single bottom plate and the at least two cover plates are formed as one single cover plate. The arrangement may for instance have the format of an object carrier or of a multi-well plate, i.e. it may have a size of particularly 86 mm×128 mm. The observation chambers and/or respective inlets/outlet or through holes of the individual microfluid devices may preferably be arranged in the grid of a 96, 384 or 1536-well plate, i.e. with distances of 9 mm, 4.5 mm or 2.25 mm.

The arrangement may for instance comprise a bottom plate and a cover plate, which are connected to one another in a liquid-tight manner, wherein the cover plate comprises recesses, which form at least two observation chambers and at least four reservoirs, wherein the observation chambers connect at least two reservoirs, the microfluid device can be filled and the cross-sectional surface of the observation chamber at the aperture of the observation chamber into one of the reservoir is at least 5 times, preferably at least 20 times smaller than the maximum cross-sectional surface of the reservoir in parallel to this cross-sectional surface of the observation chamber.

The invention further refers to a method of producing diffusively built gradients, comprising the following steps:

providing a microfluid device with two reservoirs and one observation chamber, which connects the reservoirs, particularly a microfluid device, as described above.

filling the reservoirs and the observation chamber with a neutral liquid, adding a chemical solution of a known concentration into a reservoir of the microfluid device;

liquid-tight locking of the reservoir so that in the case of a pressure load of the liquid in the reservoir with 10 times its weight the absolute compression in the reservoir is a maximum of 10% of the volume of the observation chamber, wherein the microfluid device is formed such that a diffusive gradient stable over at least two days is built up.

A neutral liquid is basically any liquid, that does not cause a chemical reaction with another liquid (a chemical solution, the chemokine) and/or the biological components of the sample. The chemokine may particularly solved in the liquid, which is filled into one of the two reservoirs of the microfluid device and thus it can diffuse into the observation chamber. The neutral liquid may for instance be purest water or an especially mixed cell culture medium, which does not have certain components, such as FCS.

The liquid that is located in a reservoir after adding a chemical solution, comprises the neutral liquid in the reservoir and the chemical solution in this reservoir. The weight of this liquid is its weight on earth's surface.

If a gradient is stable over at least two days, its incline changes within 48 hours by not more than 8%, particularly by not more than 5%.

Additionally, the above-mentioned method may comprise the following step:

filling the observation chamber with cells.

It is possible that the filling of the observation chamber with cells takes place before filling with the neutral liquid. It is additionally also possible that a further filling of the observation chamber with cells is carried out.

Within the above-mentioned method, the microfluid device may particularly be provided with two reservoirs and one observation chamber, wherein the volume of each reservoir is at least 100 times, particularly at least 200 times larger than the volume of the observation chamber and/or the cross-sectional surface of the observation chamber at the aperture of the observation chamber into one of the reservoirs is at least 5 times, particularly at least 20 times, smaller than the minimum cross-sectional surface of the reservoir in parallel to this cross-sectional surface of the observation chamber and/or the length of the observation chamber is between 100 µm and 5 mm, particularly between 500 µm and 3 mm.

The above-described microfluid device may particularly be used for examining cell migrations, particularly in diffusively built gradients.

The invention also comprises a microfluid device, particularly one of the above described microfluid devices, comprising a bottom plate and a cover plate, wherein the cover plate comprises a recess and is connected to the bottom plate in a liquid-tight manner so that the recess forms an observation chamber, wherein the observation chamber is partially filled with a gel. The gel may preferably be a matrigel, collagen gel or agarose (e.g. SeaPrep® Agarose). The observation chamber may particularly have a cross-sectional surface between 0.05 mm$^2$ and 0.4 mm$^2$, preferably between 0.075 mm$^2$ and 0.1 mm$^2$, and a length between 0.5 mm and 5 mm, preferably between 1 mm and 2.5 mm.

The invention further refers to a method of producing the above-mentioned microfluid device, comprising the following steps:

providing a bottom plate and a cover plate, wherein the cover plate has recesses;

partially filling with recesses with a gel;

liquid-tight connection of the bottom and cover plate.

The method may preferably comprise the additional step:

filling a recess, particularly by an inlet/outlet, with cells.

The filling of the recesses with a gel may be achieved for instance in that the recesses are brushed or printed with a gel, e.g. by micro-contact printing, wherein the die may consist of PDMS (polydimethylsiloxane), a 2-component silicone.

In an advantageous development, the cover plate may have several recesses so that at least two reservoirs and one observation chamber, which connects the reservoirs, are formed. The inlet/outlet may particularly lead through the over plate into a reservoir, and the microfluid device can be fillable. The cross-sectional surface of the observation chamber at the aperture of the observation chamber into one of the reservoirs may at least be 5 times smaller, particularly at least 20 times smaller than the maximum cross-sectional surface of the reservoir in parallel to this cross-sectional surface of the observation chamber. This development may further comprise one or a plurality of features of the above-described microfluid devices.

An advantage of this microfluid device and the associated method is that the gel in the observation chamber may simulate a natural environment for the cells and thus its migration may take place under comparatively real conditions. A further advantage is the fact that the cells do not have to be filled into the observation chamber simultaneously with the gel but that the cells can be filled in aqueous medium, which simplifies feasibility of the experiment particularly in the case of small liquid volumes.

BRIEF DESCRIPTION OF THE DRAWINGS

Further advantages and features will now be described exemplarily by means of the Figures.

The microfluid device according to the invention and the respective method for producing diffusively built gradients will now be explained by means of the examples shown in FIGS. 1 to 11.

DETAILED DESCRIPTION OF THE INVENTION

Figure 1:
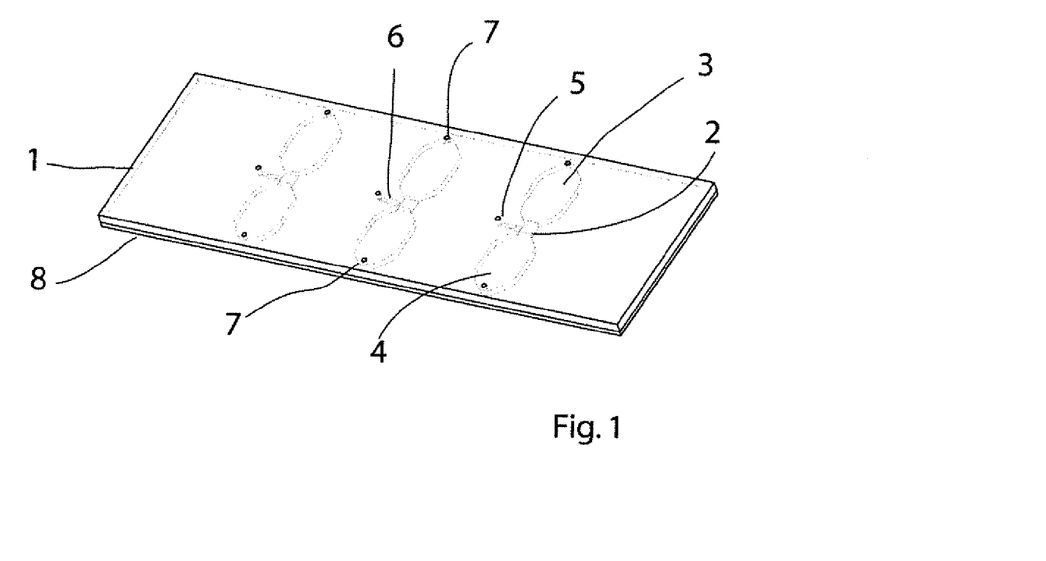
FIG. 1 shows an example for an arrangement of three microfluid devices for producing diffusively built gradients with two reservoirs each, one processing chamber and one channel

The arrangement in FIG. 1 has approximately the outer dimensions of an object carrier and comprises a cover plate 1 and a bottom plate 8 with three microfluid devices with two reservoirs 3 and 4 each, one observation chamber 2 and one channel 6. The first reservoir 3 serves as a depression and the second reservoir 4 serves as a source for the chemokine. The observation chamber 2 connects the reservoirs 3 and 4 and has a substantially smaller height than the reservoirs 3 and 4. In the observation chamber the reactions e.g. of cells onto the gradients produced by diffusion between depression and source are observed. First of all, the cells are filled in the inlet/outlet 5 through the channel 6 into the observation chamber. This takes place in that only the observation chamber is filled with cell suspension. After that the inlet/outlet 5 is locked in a liquid-tight and air-tight manner. After a waiting period for the cell adhesion, source 4 and depression 3 are filled with a neutral liquid through the inlets/outlets 7. Then, chemokine is added into the source 4 through the inlet/outlet 7, wherein the excessive liquid is removed through the inlet/outlet 7 in the depression 3. Then, the two inlets/outlets 7 are locked in a liquid-tight and air-tight manner. In this manner, the arrangement for the chemotaxis examination is prepared.

Due to the cell migration velocity of 20 μm/h and a microscopical observation range of approx. 1 mm$^2$, the preferred observation surface, which is the bottom of the observation chamber, in this example with a 5-times enlargement with a 5×-objective, is typically 0.5 mm×0.5 mm to 3 mm×3 mm. Besides a square shape of the observation surface, any other rectangular shape may be advantageous.

Figure 2:
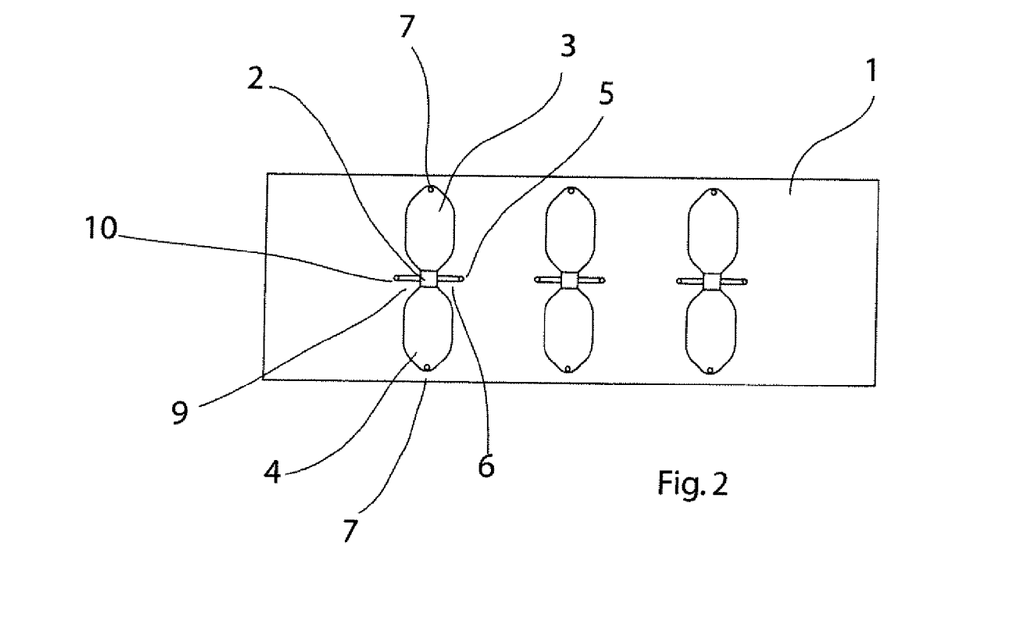
FIG. 2 is a top plan view of the arrangement according to FIG. 1 with an additional channel per microfluid device

FIG. 2 shows the same arrangement as in FIG. 1, with the exception that each microfluid device has a further channel 9 with one inlet/outlet 10 each. Through this the observation chamber 2 can be filled with cells in a more simple manner and these cells can be rinsed out in a more simple way after a certain adhesion waiting time.

Figure 3:
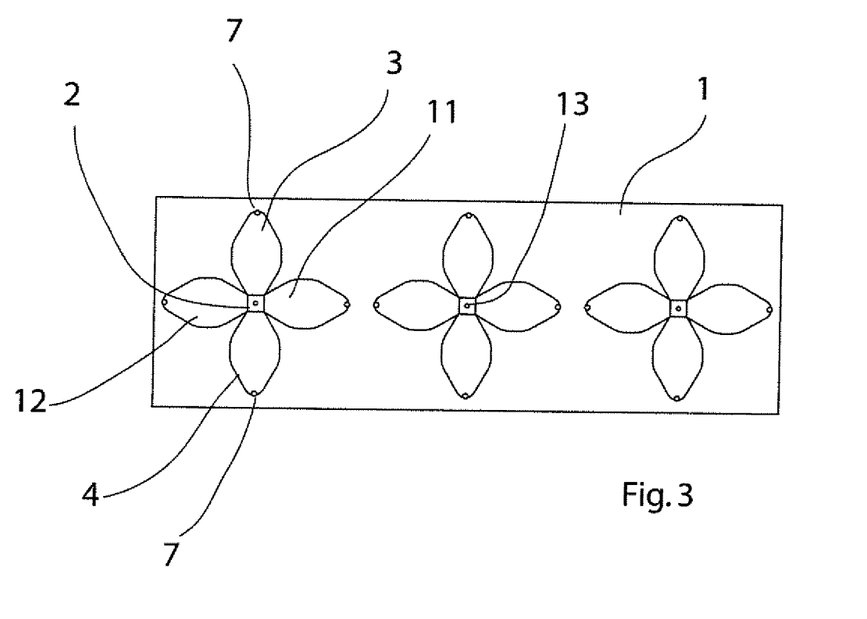
FIG. 3 shows a top plan view as an example for an arrangement of three microfluid devices for producing diffusively built gradients with four reservoirs each and one observation chamber

FIG. 3 shows an example for an arrangement for producing two diffusively built gradients arranged perpendicular with respect to one another. The arrangement comprises three microfluid devices with two depressions 3 and 1 each and two sources 4 and 12, wherein one source and one depression oppose one another. Furthermore, the observation chamber 2 lies between the reservoirs 3, 4, 11 and 12, which each have an inlet/outlet 7. To fill the observation chamber, a through hole 13 is centrally made in the center of the cover of the observation chamber.

Figure 4:
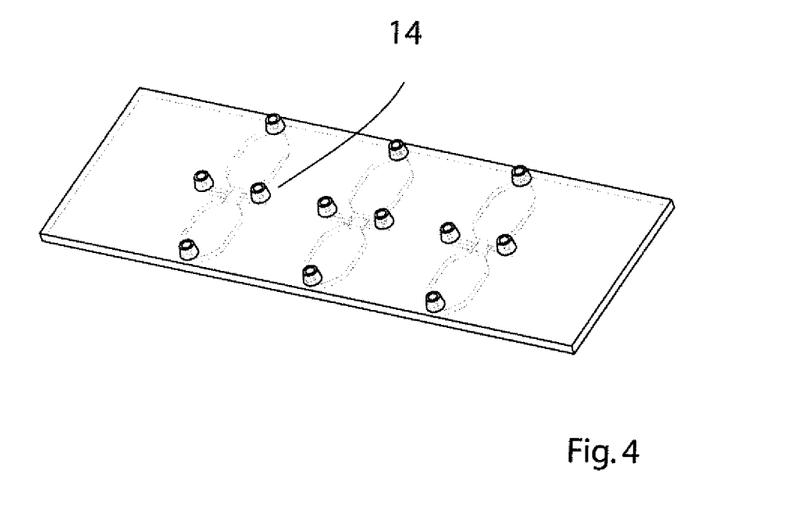
FIG. 4 shows an embodiment for inlets/outlets
Figure 5:
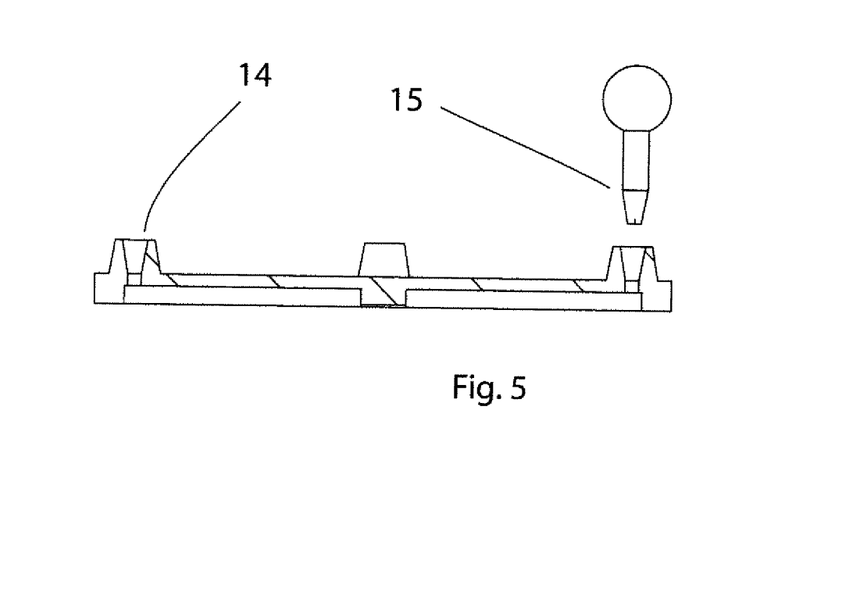
FIG. 5 is a side view of an embodiment with conical inlets/outlets

FIGS. 4 and 5 show a special embodiment 14 for the inlets/outlets 7. In this case the inlets/outlets taper conically in the downward direction so that these inlets/outlets can be locked in a liquid-tight and air-tight manner by a respective plug 15 that is also shaped conically.

Figure 6:
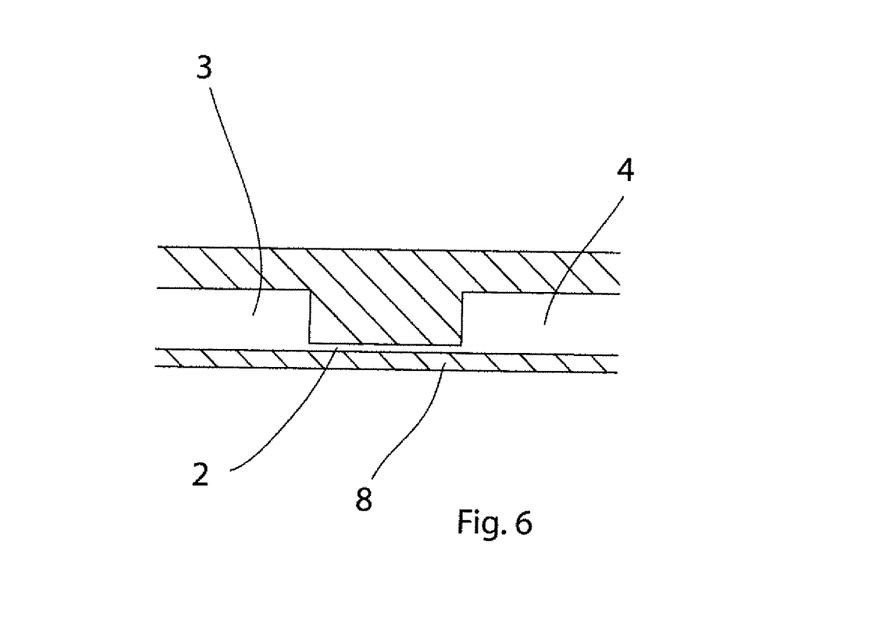
FIG. 6 is a section of a side view of a microfluid device with two reservoirs and one observation chamber

FIG. 6 is an enlarged view of a cross-section of a microfluid device with two reservoirs 3 and 4 and one observation chamber 2 between the reservoirs 3 and 4. Both reservoirs 3 and 4 are significantly greater than the observation area 2, the cross-section of the observation chamber 2 is therefore much smaller than the cross-sections of the reservoirs 3 and 4, which leads to a slowly diffusive concentration compensation between the reservoirs.

FIG. 7a is a top plan view onto the observation area 2. The source 4 adjoins on the left-hand side, on the right-hand side the depression 3 (not shown) adjoins. On the observation area, oblong surfaces 16 for cell adhesion are located, which were prepared by a surface structuring and/or treatment (Figure left). The rest of the surface is not only suitable for a cell adhesion. The cells 17 are flushed into the observation chamber (e.g. via a channel 6). After a waiting period for the adhesion, the non-adhered cells are rinsed out of the area (e.g. via a channel 10) so that only the surface 16 is homogeneously sowed with cells (Figure in the middle). Now the chemokine is added to the source 4. After a waiting period between 12 and 48 hours, a microscopic recording is made to control whether the cell density has increased caused by chemotaxis on the side of the areas 16 facing the source 4 (Figure right).

Figure 7:
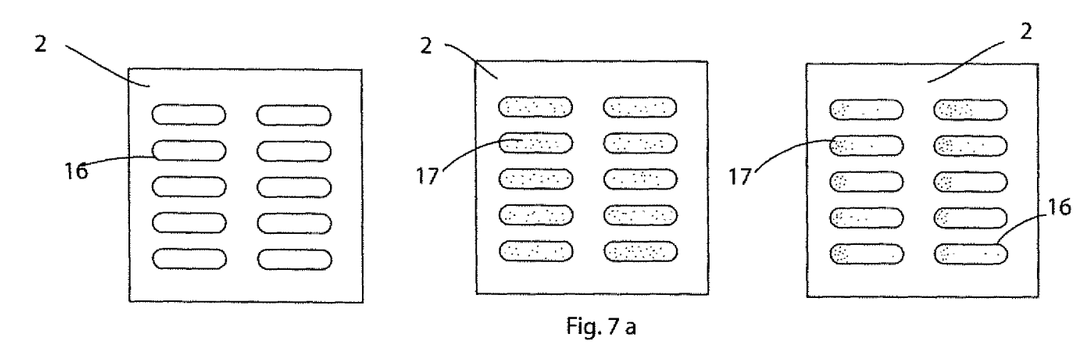
FIG. 7*a* is a top plan view onto an observation chamber with two-column cell adhesion surfaces
FIG. 7*b* is a top plan view onto an observation chamber with single-column cell adhesion surfaces
FIG. 7*c* is a top plan view onto an observation chamber with rhombical cell adhesion surfaces
FIG. 7*d* is a top plan view onto an observation chamber with triangular cell adhesion surfaces
Figure 7B:
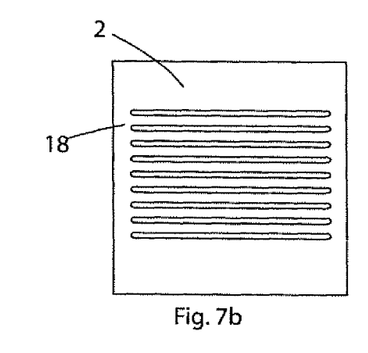
Figure 7C:
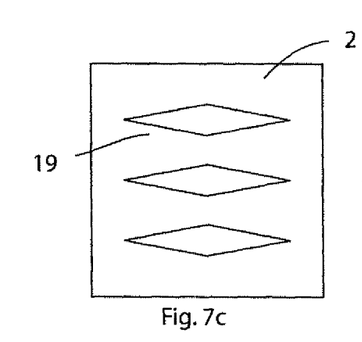
Figure 7D:
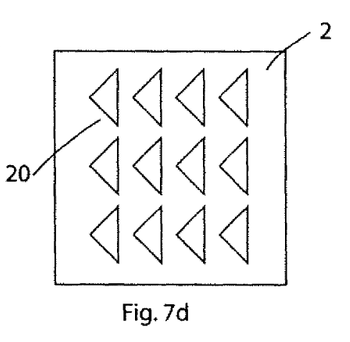

FIGS. 7b, 7c and 7d show the observation chamber 2 as in FIG. 7a, only that either long strips 18 or rhombical or triangular surfaces 19 and 20 are functionalized, i.e. surface-treated, for the cell adhesion. In FIG. 7b the width of the strips is chosen such that the cells can adhere only one after the other on a line. By such structures the cell migration can be estimated by the mere eye, i.e. without a microscope after coloring with crystal violet or the like.

The advantage of the above observation chamber, these are preferably the channels, is that during the filling process the cells distribute homogeneously so that a homogeneous cell culture can be formed. It is important in these examples that the filling takes place quickly (i.e. within 30 seconds) and the observation chamber is not held obliquely. A slower filling could lead to the fact that only one side of the chamber is provided with cells. The homogeneous distribution of the cells can be important in chemotactic experiments, particularly if the cells tend to mutually influence one another, which can be minimized with a homogeneous distribution.

Figure 8:
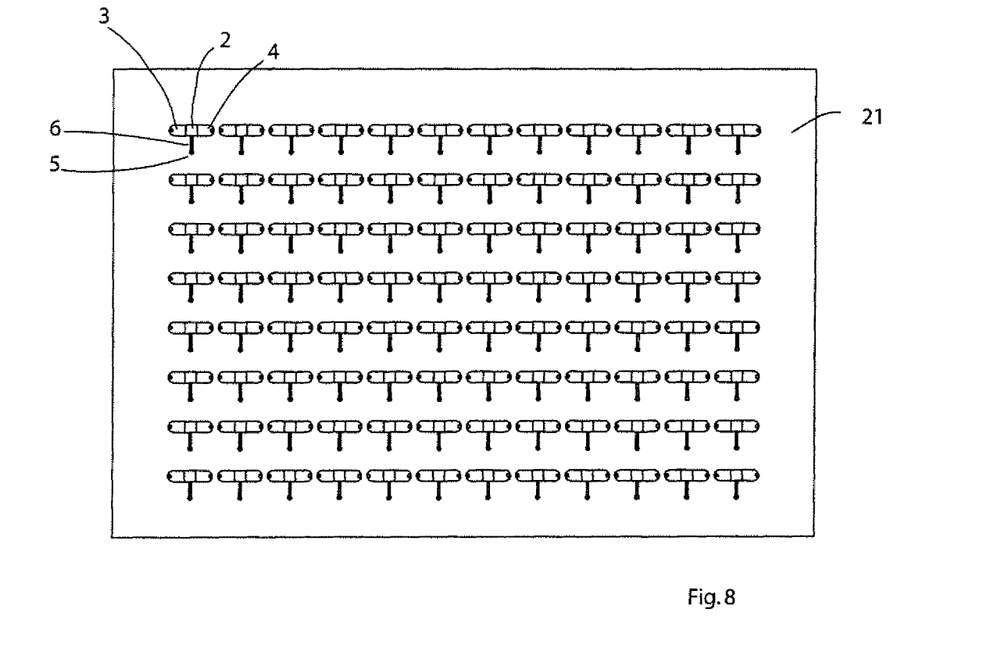
FIG. 8 is a top plan view onto an arrangement of 96 microfluid devices for producing diffusively built gradients with two reservoirs each, one observation chamber and one channel

FIG. 8 shows an arrangement with a cover plate 21 in the format of a 96-well plate. The centers of the observation chamber 2 are arranged in a square grid with a grid distance of 9 mm. The arrangement comprises eight rows with twelve microfluid devices each, wherein each microfluid device comprises one observation chamber 2, two reservoirs 3 and 4 and one channel 6. A chemotaxis experiment can be carried out in each microfluid device—independent of the other microfluid devices.

Figure 9:
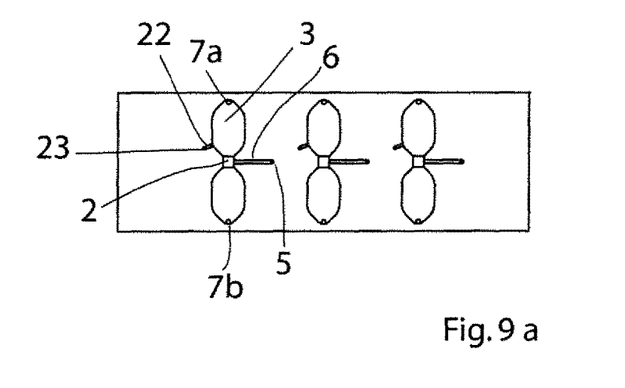
FIG. 9*a* is a top plan view as an example for an arrangement of three microfluid devices for producing diffusively built gradients with two reservoirs each, one observation chamber, one channel and one additional channel
FIG. 9*b* is a perspective view of the arrangement of FIG. 9*a*

FIG. 9 shows a microfluid device of FIG. 1 with an additional channel 22 and an additional opening 23. Thus, it is possible to rinse through the reservoir volume without destroying the diffusive gradient in the observation chamber 2. For this purpose the inlet/outlet 7a of the first reservoir 3 is opened and the inlet/outlet 7b of the second reservoir and the inlet/outlet 5 of the channel 6 is left closed. By this arrangement no flow is generated in the observation chamber when rinsing over the opening 23 and the inlet/outlet 7a.

Figure 10:
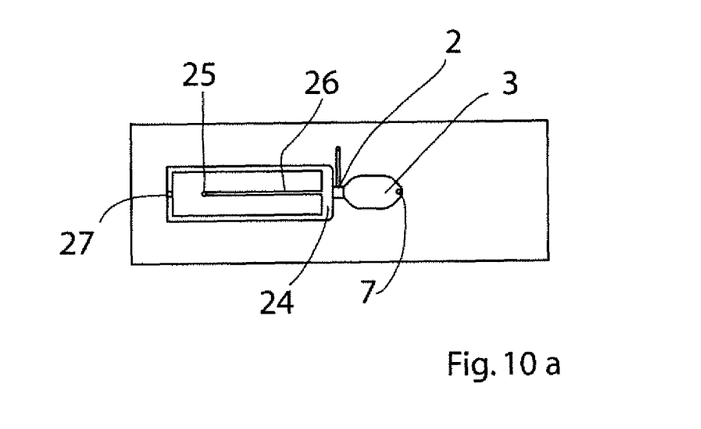
FIG. 10*a* shows a top plan view as an example for a microfluid device for producing diffusively built gradients with a reservoir, an observation chamber and a further reservoir with three channels
FIG. 10*b* is a perspective view of the microfluid device of FIG. 10*a*

FIG. 10 shows a microfluid device of FIG. 1, wherein a reservoir is replaced by a channel structure 24, 26. The channel structure has two inlets/outlets 25 and 27. If the inlets/outlets 5 and 7 are kept locked, a flow is not generated in the observation chamber 2 by a flow through the channel structure. Thus, it is possible to maintain the concentration steadily, i.e. over long periods of time by a permanent small flow or by temporary stronger flow.

Figure 11:
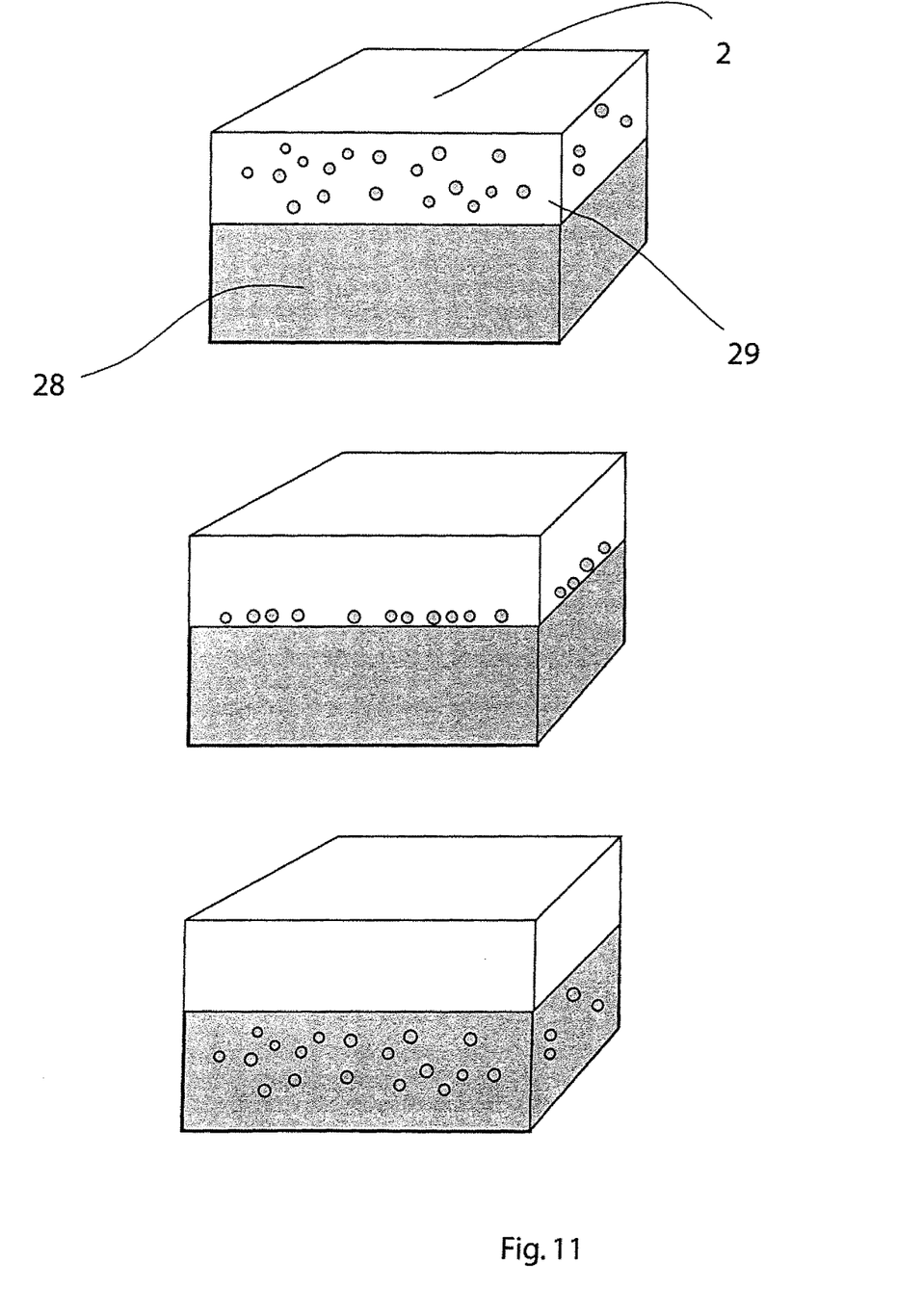
FIG. 11 shows in a perspective view an observation chamber, which is partially filled with a gel and with cells.

FIG. 11 shows the observation chamber 2 in a special design. Approximately half of the volume of the observation chamber 2 is filled with a collagen gel 28, the upper half 29 is empty in dry condition. If a cell suspension is filled into the observation chamber, the cells sink down onto the gel and actively embed therein. The cells find a natural environment therein. The migration can be observed in one dimension despite the three-dimensional embedding, since the gel influences only the temporal course but not the spatial course of the gradient in a measurable way.

Procedures to generate diffusively built gradients and the utilization thereof for further analyses will now be explained by means of four preferred embodiments.

Embodiment 1

Two reservoirs are connected through an observation chamber (channel) with a base surface of $2\times2$ mm$^2$ and a height of 0.05 mm. The height of the reservoirs is 0.8 mm and the base surface of each is approx. 1 cm$^2$. Thus, the volume of each reservoir is more than thousand times as large as the volume of the observation chamber.

The observation area is square with its base surface of a size of $2\times2$ mm$^2$, and the reservoirs adjoin on opposing sides of the square across the entire side length or the observation chamber. The bottom of the reservoir and the observation chamber lie on the same plane.

First of all, the entire microfluid device, i.e. both reservoirs and the observation chamber are filled with purest water. Then, a reservoir (which serves as a source) is filled with a fourth of the reservoir volume with four times the desired concentration of a fluorescent colorant. The liquid displaced in this way is taken from the second reservoir (which serves as a depression). Then, the two inlets/outlets of the reservoirs are locked liquid-tight and air-tight in an air bubble-free manner. Thus, the colorant does not reach the observation chamber by flow but distributes in the source only by diffusion. After some time the colorant reaches the side of the source that adjoins the observation chamber and diffuses into the observation chamber by forming a concentration gradient.

If for instance rhodamine is used as a colorant, a linear gradient between source and depression reservoir builds up in the observation chamber within 4 hours, wherein this gradient can be observed by quantitative fluorescence microscopy. The fluorescence microscopy further allows the verification that the gradient remains quasi stable over more than 48 hours, since the source concentration is diluted only to a small extent due to the low substance transport and the concentration in the depression reservoir therefore rises slowly. The concentration of the colorant in the observation chamber on the boundary surfaces to the reservoir approximately corresponds to the concentration existing in the reservoirs, and the concentration linearly drops in the observation chamber.

Embodiment 2

It is also possible with a microfluid device according to the invention having two reservoirs, one observation chamber and one channel, to carry out a simple and very reproducible preparation procedure for chemotactic migration assays.

First of all, the entire microfluid device is filled with a neutral liquid. Then, cells are flushed into the observation chamber via an inlet/outlet through a channel, where they adhere on the surface of the bottom of the observation chamber. The inlet/outlet of the channel is then locked in a liquid-tight and airtight manner by a vacuum grease.

To obtain a defined concentration of a substance in one of the reservoirs, without flooding the observation chamber, a fifth of the reservoir volume of a liquid is filled into a reservoir, which has 5 times the concentration of the actually desired concentration. Subsequently, all inlets/outlets are locked in a liquid-tight and air-tight manner by a vacuum grease.

By diffusive mixing, the desired concentration sets-in in the reservoir after approx. 30 minutes. Subsequently, the concentration gradient builds up in the observation chamber.

Embodiment 3

The statements correspond to those of embodiment 2 with the difference that directly after filling the chemokine into the reservoir, the volume of the observation chamber is filled by cooled liquid matrigel through the inlet/outlet of the channel that is not yet sealed at this time. The gel slows down the diffusion of the chemokine from the reservoir into the observation chamber, which leads to a decelerated built-up of the gradient but to a greater time stability of the gradient. Moreover, the natural three-dimensional environment of the cells is simulated in this way, as it actually takes place under real conditions.

Embodiment 4

The statements correspond to those of embodiment 2 with the difference that the cells before filling in the channel are homogeneously solved in collagen gel. Thus, the cells are located in a 3D gel matrix, which reflects the natural relations better than the 2D cell cultures. Moreover, the gel decelerates the diffusion, which leads to a delayed structure of the gradient, which, however, enhances a larger time stability of the gradient. As in embodiment 3, the natural three-dimensional environment of the cells is simulated, as it actually occurs under real conditions Pipetting Procedures For filling-in the chemokine, the droplet method is preferred. The starting point is a complete air bubble-free filled channel structure.

The precondition for this method is the same surface composition and geometry of the filling apertures. In order to introduce the chemokine into a reservoir via a first inlet/outlet, a large drop (approx. 5-fold volume of the chemikine-containing liquid) of the liquid without chemokine is applied onto the second inlet/outlet of the reservoir. Subsequently, the chemokine to be introduced is slowly pipetted in small droplets onto the first inlet/outlet of the reservoir. The surface tension of the small droplet presses the chemokine into the structure. Subsequently, the excessive liquid is taken off on the second inlet/outlet and the structure is locked in a liquid-tight and air-tight manner.

This hydrostatic method may be supported by a physical surface treatment (plasma). If the surface of the inlet/outlet is hydrophilic (small contact angle) for the large droplet and the surface at the chemokine inlet/outlet is hydrophobic (large contact angle), the chemokine-containing liquid volume will be sucked in very easily. In this case, the pipetting procedure is simplified, since the volume differences between the large and the small drop may be much smaller.

The invention claimed is:

1. A method of producing diffusively built gradient, comprising the following steps:
   providing a microfluid device with two reservoirs and one observation chamber, which connects the reservoirs, wherein the microfluid device comprises a bottom plate and a cover plate, wherein the cover plate has recesses and is connected in a liquid-tight manner with the bottom plate so that the recesses form the two reservoirs and the observation chamber, wherein one of the reservoirs can be filled, and wherein the cross-sectional surface of the observation chamber at the aperture of the observation chamber into one of the reservoirs is at least five times smaller than the maximum cross-sectional surface of the reservoir parallel to this cross-sectional surface of the observation chamber;
   filling the reservoirs and the observation chamber with a neutral liquid;
   adding a chemical solution of a known concentration into a reservoir of the microfluid device; and
   air-tight locking of the reservoir.

2. The method as claimed in claim 1, which additionally comprises the following step:
   filling the observation chamber with cells, wherein particularly the filling with cells takes place after the filling with the neutral liquid and before adding the defined concentrated chemical solution.

3. The method as claimed in claim 1, wherein the microfluid device is provided with two reservoirs and one observation chamber, wherein the volume of each reservoir is at least 100 times, particularly at least 200 times larger than the volume of the observation chamber and/or the cross-sectional surface of the observation chamber at the aperture of the observation chamber into one of the reservoirs is at least 5 times, particularly at least 20 times smaller than the maximum cross-sectional surface of the reservoir in parallel to this cross-sectional surface of the observation chamber and/or the length of the observation chamber is between 100 µm and 5 mm, particularly between 500 µm and 3 mm.

4. The method as claimed in claim 1, wherein the reservoir is locked in an air bubble free manner.

5. The method as claimed in claim 1, wherein the observation chamber is at least partially filled with a gel.

6. A method of producing diffusively built gradient, comprising the following steps:
   providing a microfluid device with two reservoirs and one observation chamber, which connects the reservoirs, wherein the microfluid device comprises a bottom plate and a cover plate, wherein the cover plate has recesses and is connected in a liquid-tight manner with the bottom plate so that the recesses form the two reservoirs and the observation chamber, wherein one of the reservoirs can be filled, and wherein the cross-sectional surface of the observation chamber at the aperture of the observation chamber into one of the reservoirs is at least five times smaller than the maximum cross-sectional surface of the reservoir parallel to this cross-sectional surface of the observation chamber;

filling the reservoirs and the observation chamber with a neutral liquid;

adding a chemical solution of a known concentration into a reservoir of the microfluid device; and liquid-tight locking of the reservoir.

7. The method as claimed in claim 6, which additionally comprises the following step:

filling the observation chamber with cells, wherein particularly the filling with cells takes place after the filling with the neutral liquid and before adding the defined concentrated chemical solution.

8. The method as claimed in claim 6, wherein the microfluid device is provided with two reservoirs and one observation chamber, wherein the volume of each reservoir is at least 100 times, particularly at least 200 times larger than the volume of the observation chamber and/or the cross-sectional surface of the observation chamber at the aperture of the observation chamber into one of the reservoirs is at least 5 times, particularly at least 20 times smaller than the maximum cross-sectional surface of the reservoir in parallel to this cross-sectional surface of the observation chamber and/or the length of the observation chamber is between 100 μm and 5 mm, particularly between 500 μm and 3 mm.

9. The method as claimed in claim 6, wherein the reservoir is locked in an air bubble free manner.

10. The method as claimed in claim 6, wherein the observation chamber is at least partially filled with a gel.

11. A method of producing diffusively built gradient, comprising the following steps:

providing a microfluid device with two reservoirs and one observation chamber, which connects the reservoirs, wherein the microfluid device comprises a bottom plate and a cover plate, wherein the cover plate has recesses and is connected in a liquid-tight manner with the bottom plate so that the recesses form the two reservoirs and the observation chamber, wherein one of the reservoirs can be filled, and wherein the cross-sectional surface of the observation chamber at the aperture of the observation chamber into one of the reservoirs is at least five times smaller than the maximum cross-sectional surface of the reservoir parallel to this cross-sectional surface of the observation chamber;

filling the reservoirs and the observation chamber with a neutral liquid;

adding a chemical solution of a known concentration into a reservoir of the microfluid device; and air-tight and liquid-tight locking of the reservoir.

12. The method as claimed in claim 11, which additionally comprises the following step:

filling the observation chamber with cells, wherein particularly the filling with cells takes place after the filling with the neutral liquid and before adding the defined concentrated chemical solution.

13. The method as claimed in claim 11, wherein the microfluid device is provided with two reservoirs and one observation chamber, wherein the volume of each reservoir is at least 100 times, particularly at least 200 times larger than the volume of the observation chamber and/or the cross-sectional surface of the observation chamber at the aperture of the observation chamber into one of the reservoirs is at least 5 times, particularly at least 20 times smaller than the maximum cross-sectional surface of the reservoir in parallel to this cross-sectional surface of the observation chamber and/or the length of the observation chamber is between 100 μm and 5 mm, particularly between 500 μm and 3 mm.

14. The method as claimed in claim 11, herein the reservoir is locked in an air bubble free manner.

15. The method as claimed in claim 11, wherein the observation chamber is at least partially filled with a gel.

16. The method of claim 1, wherein the observation chamber provides fluid communication between the reservoirs on respective at least two first sides of the observation chamber.

17. The method of claim 1, wherein the microfluid device further comprises at least one channel in fluid communication with the observation chamber at a respective at least one second side of the observation chamber different than the first sides.

18. The method of claim 1, wherein the observation chamber includes at least one cell adhesion surface.

* * * * *